(12) United States Patent
Yang

(10) Patent No.: US 11,234,858 B2
(45) Date of Patent: Feb. 1, 2022

(54) BODY FLUID COLLECTION DEVICE

(71) Applicant: Kuohuang Yang, Taiwan (CN)

(72) Inventor: Kuohuang Yang, Taiwan (CN)

( * ) Notice: Subject to any disclaimer, the term of this patent is extended or adjusted under 35 U.S.C. 154(b) by 271 days.

(21) Appl. No.: 16/477,528

(22) PCT Filed: Jan. 9, 2018

(86) PCT No.: PCT/CN2018/000012
§ 371 (c)(1),
(2) Date: Jul. 12, 2019

(87) PCT Pub. No.: WO2018/130103
PCT Pub. Date: Jul. 19, 2018

(65) Prior Publication Data
US 2019/0358080 A1    Nov. 28, 2019

(30) Foreign Application Priority Data

Jan. 12, 2017  (CN) .......................... 201710021718.2
Jan. 4, 2018  (CN) .......................... 201810008717.9

(51) Int. Cl.
*A61F 6/04*  (2006.01)
*A61B 10/00*  (2006.01)

(52) U.S. Cl.
CPC ............ *A61F 6/04* (2013.01); *A61B 10/0058* (2013.01); *A61F 2006/047* (2013.01)

(58) Field of Classification Search
CPC ................ A61B 5/0088; A61B 1/0684; A61B 2090/306; A61B 5/682; A61B 1/00096; A61B 6/145; A61B 10/0058; A61B 10/00; A61C 7/08; A61C 8/0001; A61C 1/088; A61C 13/087; A61F 6/065; A61F 2006/042; A61F 6/04; A61F 6/146; A61F 6/06; Y10S 128/918

See application file for complete search history.

(56) References Cited

U.S. PATENT DOCUMENTS 5,458,114 A  *  10/1995  Herr .......................... A61F 6/04
                                                                      128/842

FOREIGN PATENT DOCUMENTS

CN          1035430 A       9/1989
CN          2086596 U      10/1991
(Continued)

OTHER PUBLICATIONS

Written Opinion and International Search Report of International Patent Application No. PCT/CN2018/000012.

*Primary Examiner* — Ophelia A Hawthorne
(74) *Attorney, Agent, or Firm* — JCIP; Joseph G. Chu; Jeremy I. Maynard

(57) ABSTRACT

The present invention discloses a body fluid collection device, so as to provide a body fluid collection device which is easy to adhere to a human body, preventing peeling off, and capable of collecting a body fluid such as urine or semen. The body fluid collection device of the present invention includes: a fitting part, which is a sheet having an opening and has a first surface and a second surface; an adhesive layer, disposed on the first surface of the fitting part; and a collection film having an edge having a circumference greater than a circumference of the opening of the fitting part and connected to the second surface of the fitting part in a manner of surrounding the opening of the fitting part. The present invention relates to the technical field of body fluid collection device.

20 Claims, 9 Drawing Sheets

(56) References Cited

FOREIGN PATENT DOCUMENTS

| | | | |
|---|---|---|---|
| CN | 2117865 U | 10/1992 | |
| CN | 2702722 Y | 6/2005 | |
| CN | 101036605 A | 9/2007 | |
| CN | 204971790 U | 1/2016 | |
| FR | 2750854 A1 * | 1/1998 | ............ A61F 6/065 |
| WO | 0062723 A1 | 10/2000 | |
| WO | 2014041534 A1 | 3/2014 | |
| WO | 2014178661 A1 | 11/2014 | |

* cited by examiner

BODY FLUID COLLECTION DEVICE

BACKGROUND

Technical Field

The present invention relates to a liquid collection device, and more particularly to a body fluid collection device.

Related Art

For men confined to bed, collecting urine samples using conventional urine cups or test tubes can easily stain mattresses. In a conventional process of semen analysis, it is very difficult for a man to accurately inject semen into a small container while masturbating, often resulting in collection volume insufficient to be tested. Conventional condoms reduce the willingness of men to contraception because they block direct contact of sexual mucosae between men and women. Therefore, how to provide a body fluid collection device capable of collecting body fluids such as urine or semen, overcoming the deficiencies of prior art described above and storing semen without detracting from the user's sexual pleasure when serving as a male contraceptive device is an important problem to be solved.

SUMMARY

In view of the above problems, one of the objectives of the present invention is to provide a body fluid collection device which is easy to adhere to a human body, preventing peeling off, and capable of collecting a body fluid such as urine or semen that is less prone to leakage to cause contamination. Further, one implementation of the body fluid collection device of the present invention is a male contraceptive device which can store semen without detracting from sexual pleasure of a user.

The body fluid collection device according to one embodiment of the present invention includes: a fitting part, which is a sheet having an opening and has a first surface and a second surface; an adhesive layer, disposed on the first surface of the fitting part; and a collection film having an edge, the edge having a circumference greater than a circumference of the opening of the fitting part and connected to the second surface of the fitting part in a manner of surrounding the opening of the fitting part. In other words, the collection film and at least a part of the fitting part, on which the opening is located, form a storage space.

In the body fluid collection device according to one embodiment of the present invention, a joint of the edge of the collection film and the second surface of the fitting part has a width, an inner edge of the joint forms a connecting rim surrounding the opening, the connecting rim has a circumference greater than the circumference of the opening such that the fitting part is divided into an inner portion and an outer portion, the inner portion of the fitting part and the collection film form a storage space having an opening, and the storage space is capable of storing the body fluid of the user.

In the body fluid collection device according to one embodiment of the present invention, the collection film may have a pocket structure, the pocket structure having an open end defined by the edge of the collection film. In the body fluid collection device according to one embodiment of the present invention, the body fluid collection device may further include a retaining part, which is a planar or radially curved sheet and is provided with at least one retaining part opening, an outer edge of the retaining part being connected to the outer side of the pocket structure close to the open end.

In the body fluid collection device according to one embodiment of the present invention, the collection film may include: an annular part, which is a planar or radially curved annular film, an outer edge of the annular part being the edge of the collection film; a pocket part, having a pocket part open end, the pocket part open end being connected to an inner surface of the annular part, wherein the pocket part open end of the pocket part has a circumference greater than a circumference of an inner edge of the annular part, and is connected to the inner surface of the annular part at a distance from the inner edge of the annular part.

In the body fluid collection device according to one embodiment of the present invention, the collection film has a pocket structure, the pocket structure having a connecting hole and an open end defined by the edge of the collection film, and a drainage tube being connected to the connecting hole.

In the body fluid collection device according to one embodiment of the present invention, the collection film may be a planar or curved elastic film. In other words, by means of the elasticity of the collection film, the collection film can form a storage space with at least a part of the fitting part, the opening being located on said at least a part of the fitting part.

In the body fluid collection device according to one embodiment of the present invention, the edge of the collection film is connected to the second surface of the fitting part along a circle, an ellipse or a rounded regular polygon. In the body fluid collection device according to one embodiment of the present invention, the opening of the fitting part is located at the center of the circle, the ellipse or the rounded regular polygon.

In the body fluid collection device according to one embodiment of the present invention, the fitting part in natural state (i.e. not in use) is a planar sheet or a curved sheet.

In the body fluid collection device according to one embodiment of the present invention, the edge of the collection film is not in contact with an outer edge of the fitting part.

In the body fluid collection device according to one embodiment of the present invention, the opening is located on a long symmetry axis of the fitting part, and the distances between the opening and the two outer edges of the fitting part on the long symmetry axis may be unequal.

In the body fluid collection device according to one embodiment of the present invention, the fitting part is a rounded polygon having a symmetry axis and a first side and a second side perpendicular to the symmetry axis, a length of the first side being not equal to a length of the second side, and the opening being located on the symmetry axis.

In the body fluid collection device according to one embodiment of the present invention, the shape of the fitting part is a circle, an ellipse or a rounded polygon.

In the body fluid collection device according to one embodiment of the present invention, an edge of the fitting part has a notch, and the notch may preferably be, for example, an arc shape notch.

In the body fluid collection device according to one embodiment of the present invention, the body fluid collection device further includes a structure holding part extending along the edge of the fitting part. A part of an outer edge of the structure holding part is further extendable outwards to form at least one fin protruding from the fitting part for the user to grip with fingers.

In the body fluid collection device according to one embodiment of the present invention, the body fluid collection device further includes a gripping part having at least one point connected to the structure holding part and foldable to be flattened to the fitting part before use.

In the body fluid collection device according to one embodiment of the present invention, the constituent material of the adhesive layer includes a pressure-sensitive adhesive.

In the body fluid collection device according to one embodiment of the present invention, the edge of the collection film and the second surface of the fitting part may be connected by using a solvent, an adhesive, an adhesive tape or an adhesive film, or may be fusion-bonded (welded) by electrothermal heating, ultrasonic waves, high-frequency waves or the like.

In the body fluid collection device according to one embodiment of the present invention, the edge of the collection film and the fitting part are formed integrally so as to be connected.

In the body fluid collection device according to one embodiment of the present invention, a widest part of the outer portion of the fitting part may be greater than 2 mm, or greater than a circumference of the connecting rim divided by 31.4.

The advantages of the present invention include that the body fluid collection device of the present invention has a simple structure, that it is easy to adhere to the human body for use, and that it can effectively prevent the collected body fluid from leaking. For example, one embodiment of the present invention can be used as a male contraceptive device, and the device can be easily used to achieve a contraceptive effect by adhering the device to a male glans penis, thereby conveniently and safely solving the contraceptive problem of the user. Besides, in the embodiment as the male contraceptive device, the fitting part of the present invention adheres only to a part of the glans penis, so that the sexual pleasure of both men and women can be more effectively improved. Since the collection film of the present invention is not directly connected to the edge of the opening of the fitting part, that is, the joint of the edge of the collection film and the fitting part forms a connecting rim surrounding the opening, an inner portion is formed between the connecting rim and the opening of the fitting part, and this inner portion also adheres to the glans penis through the adhesive layer. This structure helps to avoid semen leakage more effectively. Based on the same structure, the present invention can also be used as a semen or urine collection device for men, and also has the effect of avoiding leakage. Through these implementations, the present invention can solve the problems arising from urine test, semen test, or contraception of the user.

DETAILED DESCRIPTION

Figure 1:
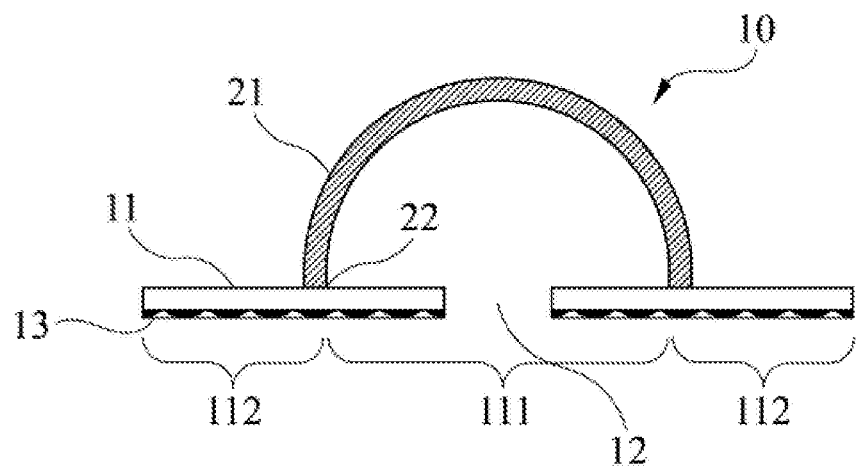
FIG. 1 is a schematic view showing one embodiment of a body fluid collection device of the present invention.

Hereinafter, embodiments of the present invention will be described with reference to the drawings, where the same or similar components are denoted by the same reference numerals.

The body fluid collection device 10 shown in FIG. 1 is one embodiment of the present invention. The body fluid collection device 10 includes a fitting part 11 having an opening 12, and a collection film 21. The fitting part 11 is a sheet having a first surface and a second surface opposite to the first surface, and an adhesive layer 13 is disposed on the first surface for adhering to a user. The collection film 21 has an edge having a circumference greater than a circumference of the opening 12 of the fitting part 11 and connected to the second surface of the fitting part 11 in a manner of surrounding the opening 12 of the fitting part 11. The edge of the collection film 21 may be connected to the second surface of the fitting part 11 along a circle, an ellipse or a rounded regular polygon. The opening 12 is located at the center of the circle, the ellipse or the rounded regular polygon. In this embodiment, the collection film 21 has a pocket structure, the pocket structure having an open end defined by the edge of the collection film 21, and the open end being connected to the second surface of the fitting part 11. The material of the collection film 21 is preferably having elasticity, but a material having no elasticity can also be used. If a material having a high elasticity is used, the collection film 21 may also be manufactured as a planar or curved film.

The body fluid collection device 10 may be manufactured by using, for example, but not limited to, natural latex, synthetic latex, rubber, silica gel, polyisoprene (PI), polyurethane (PU), polymeric materials, or biomaterials. The fitting part 11 may be, but not limited to, an elastic film which is a sheet having a planar or curved surface in a natural state, and preferably has a thickness of not more than 0.1 millimeter (mm), and the shape thereof may be, but not limited to, a circle, an ellipse or a rounded polygon. The constituent material of the adhesive layer 13 may include, for example, a pressure-sensitive adhesive. The pocket structure of the collection film 21 can be manufactured by using, for example, but not limited to, vacuum forming, compressed air forming, match mold forming, blow molding, 3D printing, or dip forming, and the thickness thereof is preferably not more than 0.1 mm. The edge of the collection film 21 and the second surface of the fitting part 11 may be connected by using, for example, but not limited to, a solvent, an adhesive, an adhesive tape or an adhesive film, or may be fusion-bonded (welded) by, for example, but not limited to, electrothermal heating, ultrasonic waves, high-frequency waves or the like. The collection film 21 may also be manufactured integrally with the fitting part 11.

As shown in FIG. 1, the joint of the edge of the collection film 21 and the second surface of the fitting part 11 has a width, the inner edge of the joint (the edge adjacent to the opening 12) forms a connecting rim 22 surrounding the opening 12, and the circumference of the connecting rim 22 is greater than the circumference of the opening 12, thereby dividing the fitting part 11 into an inner portion 111 and an outer portion 112. That is, there is a distance between the connecting rim 22 and the opening 12, the inner edge of the fitting part 11 (the edge of the opening 12) and the connecting rim 22 define the inner portion 111, and the connecting rim 22 and the outer edge of the fitting part 11 define the outer portion 112. The inner portion 111 of the fitting part 11 and the collection film 21 constitute a storage space having the opening 12, which can be used for storing the body fluid of the user. The circular connecting rim 22 and the opening 12 at the center of the circle in FIG. 1 are merely exemplified. To effectively disperse the body fluid pressure, the connecting rim 22 may also be configured as another regular shape, for example, a rounded regular polygon, preferably a circle or an ellipse, and the opening 12 is not limited to being located at the center of the area surrounded by the connecting rim 22.

Figure 2A:
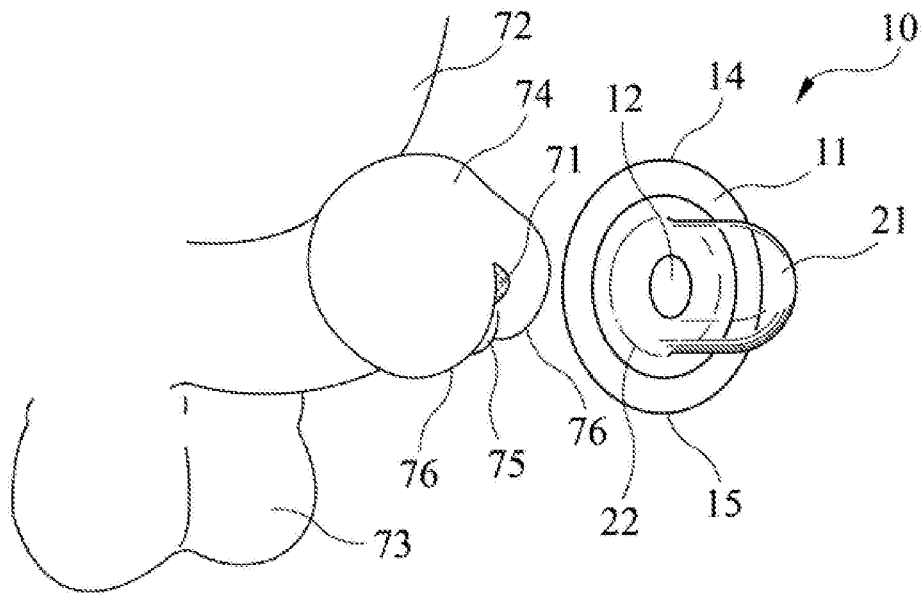
FIG. 2A is a schematic view showing a use mode of one embodiment of the body fluid collection device of the present invention.
Figure 2B:
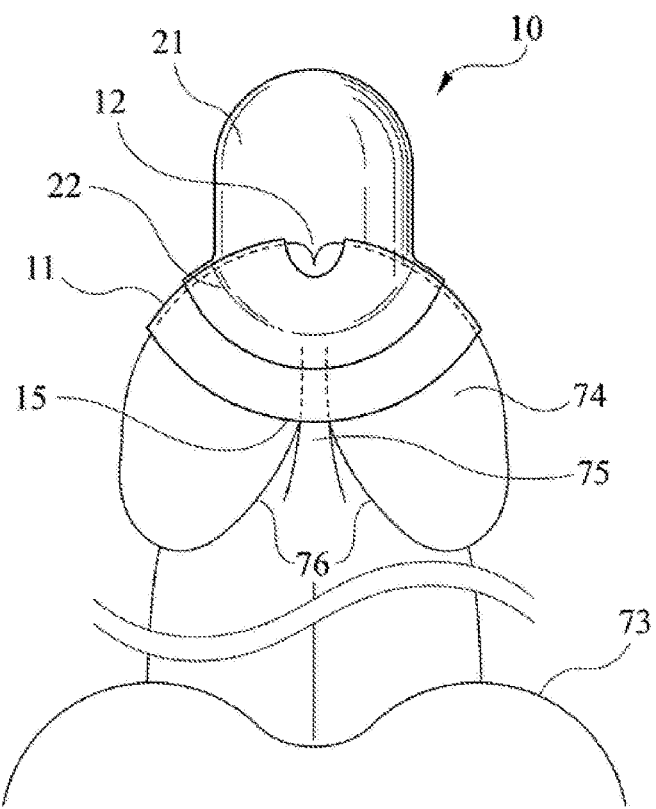
FIG. 2B is a schematic view showing a use mode of one embodiment of the body fluid collection device of the present invention.
Figure 2C:
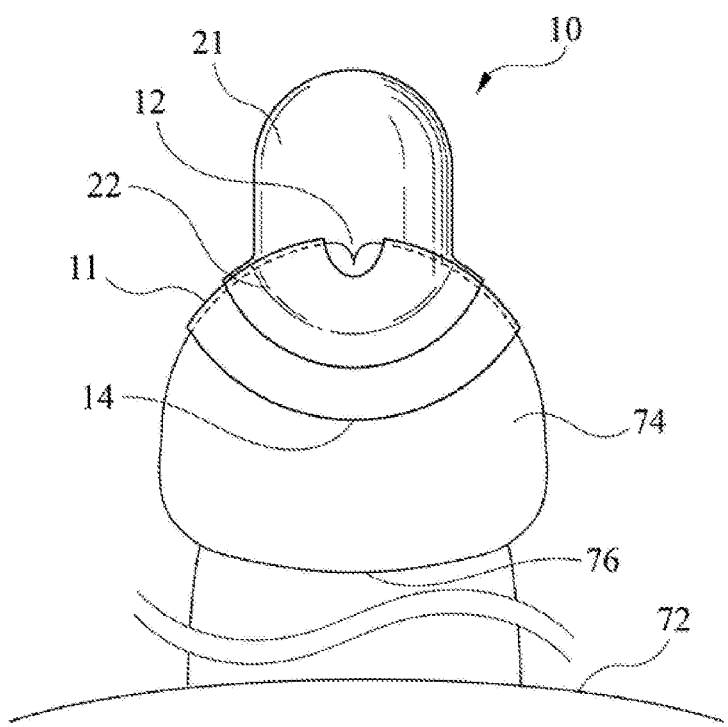
FIG. 2C is a schematic view showing a use mode of one embodiment of the body fluid collection device of the present invention.
Figure 2D:
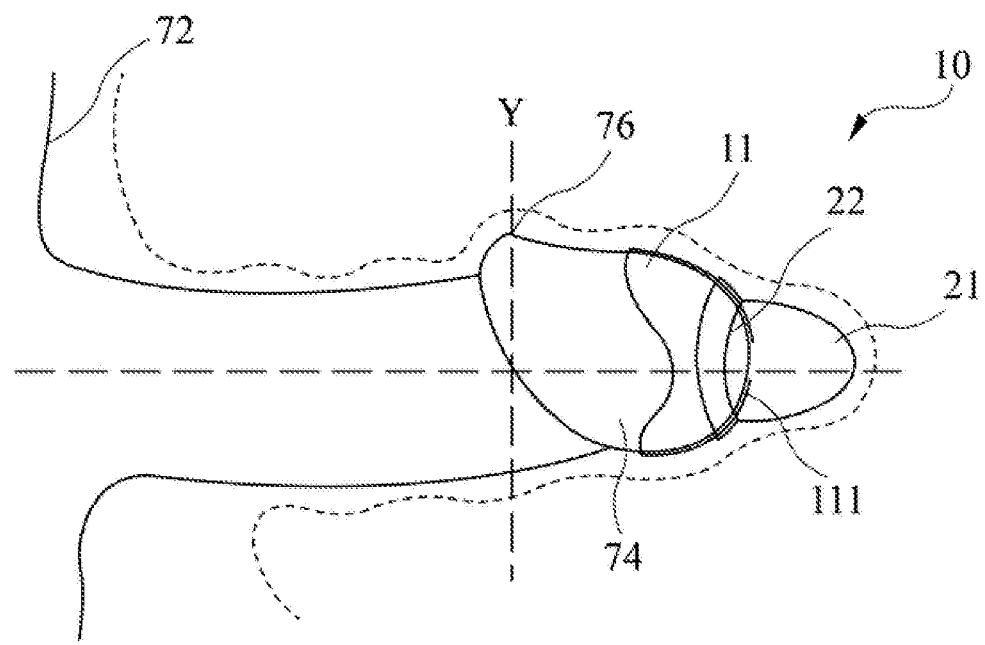
FIG. 2D is a schematic view showing a use mode of one embodiment of the body fluid collection device of the present invention.

FIG. 2A to FIG. 2D are schematic views showing a use mode of the body fluid collection device 10 from different perspectives: FIG. 2A is a three-dimensional view, FIG. 2B is a bottom view, FIG. 2C is a top view, and FIG. 2D is a side view. For example, the collection film 21 has a transparent pocket structure, the pocket structure having an open end defined by the edge of the collection film 21. In the case where the collection film 21 and the fitting part 11 are connected in a fusion manner, as shown in FIG. 2A, the open end of the collection film 21 is connected to the second surface of the circular (or elliptical) fitting part 11 along a circle (or ellipse) in a fusion manner, and the joint has a width preferably greater than or equal to 1 mm. When a user uses the body fluid collection device 10, the opening 12 is aligned with the urethra orifice 71 of the user, the top edge 14 of the fitting part 11 faces the abdomen 72 of the user, the bottom edge 15 of the fitting part 11 faces the scrotum 73 of the user, the part of the fitting part 11 from the opening 12 to the bottom edge 15 is adhered by the adhesive layer (not shown) to the frenulum 75 below the glans penis 74 and a part of the corona glandis 76 adjacent to the scrotum 73 (shown in FIG. 2B), the part of the fitting part 11 from the opening 12 to the top edge 14 is adhered by the adhesive layer to the glans penis 74 (shown in FIG. 2C), and the top edge 14 and the corona glandis 76 adjacent to the abdomen 72 may have a distance therebetween. When the present invention is used as a male contraceptive device, the nerve-filled glans penis 74 can be exposed to a larger extent, thereby increasing the user's pleasure in performing sexual behaviors. Furthermore, the elastic fitting part 11 can be applied to the glans penis 74 of different sizes or different curved surfaces in addition to easy attachment. Once the body fluid collection device 10 is torn off, the body fluid (for example, urine or semen) stored in the storage space can be poured into a test tube through the opening 12 to perform body fluid test.

The body fluid collection device 10 of the present invention is suitable for adhering to the glans penis when used as a male contraceptive device. As shown in FIG. 2D, the outer edge of the fitting part 11 should not exceed a radial vertical line Y (the vertical line Y is perpendicular to a central axis of the penis) of the corona glandis 76 passing through the adjacent abdomen 72. Therefore, the maximum width of the fitting part 11 can be, for example, less than 90 mm, preferably less than 70 mm, and more preferably less than 50 mm, so that the nerve-filled penis can be less covered. The circumference of the connecting rim 22 is less than the circumference of a general penis, for example, less than 150 mm, preferably less than 120 mm, and more preferably less than 90 mm, so that the area where the penis is covered by two layers of the materials (including the inner portion 111 of the fitting part 11 and the collection film 21) is smaller, thereby increasing the user's pleasure. The depth of the pocket of the collection film 21 is greater than the circumference of the connecting rim 22 divided by 6.28, for example greater than 10 mm, preferably greater than 20 mm, and more preferably greater than 30 mm, to accommodate more semen.

If the collection film 21 has the same shape as the fitting part 11 and the edges of the two are aligned with each other and jointed, the manufacturing process is relatively simple. However, if the edge of the collection film 21 is smaller than the outer edge of the fitting part 11, when the present invention is used as a male contraceptive device, it is possible to prevent an excessively thick edge from scratching the vaginal wall and causing discomfort to a female, and also to prevent the outer edge of the fitting part 11 from being rolled up to cause peeling due to excessive thickness. Nevertheless, the structure in which the edge of the collection film 21 is smaller than the outer edge of the fitting part 11 requires separate punching of the two, so it is much more difficult in the process such as forming, gripping, positioning (the positioning hole cannot be arranged) or connecting to the fitting part 11 of the collection film 21, especially when the collection film 21 is of a pocket structure. In one embodiment of the present invention, the edge of the collection film 21 keeps a distance from the outer edge of the fitting part 11 (i.e. not in contact with the outer edge of the fitting part 11), and the distance is preferably greater than 2 mm. As shown in FIG. 2D, since the penis expands the vagina when the sexual behavior is performed, if the diameter of the open end of the collection film 21 is substantially less than the diameter of the glans penis 74 (that is, the area of the inner portion 111 of the fitting part 11 is less than the radial cross section of the glans penis 74), the collection film 21 can be prevented from being ripped due to friction of the vaginal wall and pulling of the collection film 21 during the stroking motion.

Figure 2E:
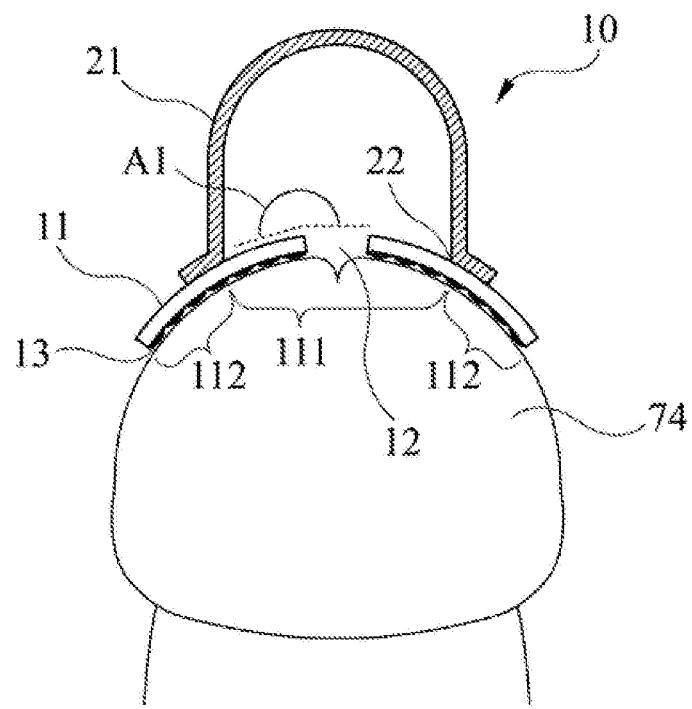
FIG. 2E is a schematic view showing a use mode and the effect of one embodiment of the body fluid collection device of the present invention.
Figure 2F:
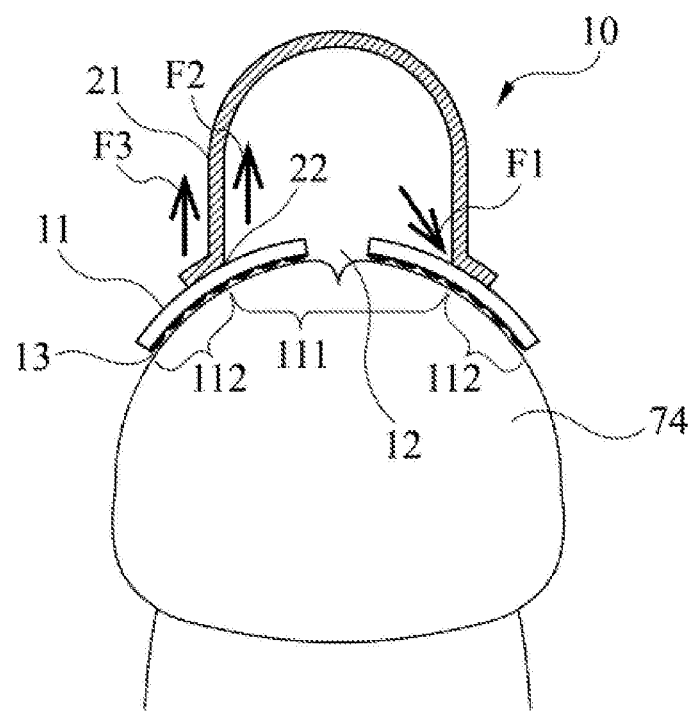
FIG. 2F is a schematic view showing a use mode and an effect of one embodiment of the body fluid collection device of the present invention.
Figure 2G:
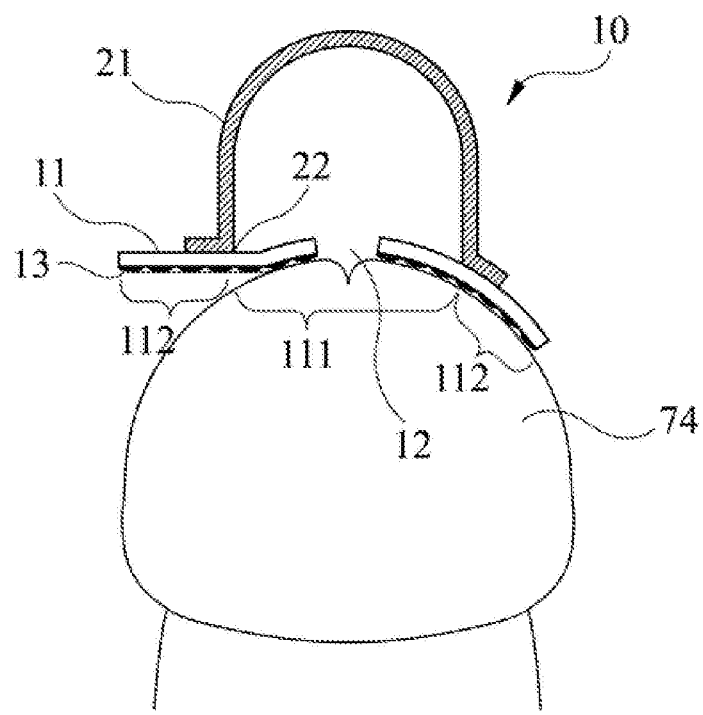
FIG. 2G is a schematic view showing a use mode and an effect of one embodiment of the body fluid collection device of the present invention.

The hydraulic pressure of the urine or semen in the storage space while the body fluid entering the storage space, or, during the sexual behavior with the present invention as a male contraceptive device, the permeation of male or female secretions, the hydraulic pressure of the prostatic fluid in the storage space, the stroking motion pulling the collection film 21, the pulling force generated by the collection film 21 on the fitting part 11 due to expansion during ejaculation, the stroking motion rubbing the edge of the fitting part 11, and other factors, may result in the fitting part 11 being peeled off from the glans penis 74 to cause leakage of body fluid. As shown in FIG. 2E to FIG. 2G, in the storage space, the inner portion 111 of the fitting part 11 is adhered to the glans penis 74 by the adhesive layer 13, so that effectively preventing the fitting part 11 from being peeled off. As shown in FIG. 2E, when the body fluid collection device 10 is in use, the fitting part 11 is adhered to the glans penis 74 by the adhesive layer 13, so that the inner portion 111 presents a curved surface facing the storage space. Therefore, inside the storage space, an angle A1 is formed between the opening 12 and body fluid collection device 10 (i.e., the inner portion 111 of the fitting part 11) immediately adjacent to the opening 12, and the angle A1 is a straight angle or a reflex angle facing the storage space. After the body fluid enters the storage space, since the angle A1 formed between the surface of the glans penis 74 and the body fluid collection device 10 is a straight angle or a reflex angle, the body fluid is less likely to leak from the opening 12 along a gap between the fitting part 11 and the glans penis 74 towards the edge of the fitting part 11.

As shown in FIG. 2F, a closed structure formed by the inner portion 111 of the fitting part 11 adhering to the glans penis 74 and the collection film 21 can withstand the pressure F1 of the body fluid and/or internal air, so that the body fluid in the storage space is less likely to leak from the edge of the fitting part 11. The inner portion 111 and the outer portion 112 of the fitting part 11 are adhered to the glans penis 74 by the adhesive layer 13, and with the connecting rim 22 as a reference point, a bilateral fixing effect is generated on the inner side and the outer side respectively, thereby offsetting the pulling force generated by the collection film 21 which is expanded when filled with body fluid and/or air against the fitting part 11 (for example, the pulling force F2 shown in FIG. 2F), and the pulling force generated by the piston motion pulling the collection film 21 against the fitting part 11 when the present invention is used as a male contraceptive device (for example, the pulling force F3 shown in FIG. 2F). To achieve a better bilateral fixing effect, the widest part of the outer portion 112 of the fitting part 11 may, for example, have a width greater than 2 mm, preferably greater than 4 mm, more preferably greater than 6 mm, or greater than the circumference of the connecting rim 22 divided by 31.4.

As shown in FIG. 2G, during the sexual behavior, due to the permeation of the female vaginal secretion or lubricating fluid and the friction or pulling of the piston motion, the fitting part 11 may be peeled off from the glans penis 74 in a direction from the edge to the opening 12. However, even if the outer portion 112 of the fitting part 11 is peeled off and the inner portion 111 is partially peeled off, as long as the inner portion 111 adjacent to the opening 12 still partially adheres to the glans penis 74, the semen in the storage space will not leak.

According to the above description, the body fluid collection device 10 of the present invention has a simple structure and has the functions of collecting urine, prostatic fluid and semen and being contraceptive. Other variations of the body fluid collection device of the present invention will now be described with reference to the related drawings as embodiments of a male contraceptive device.

Figure 3:
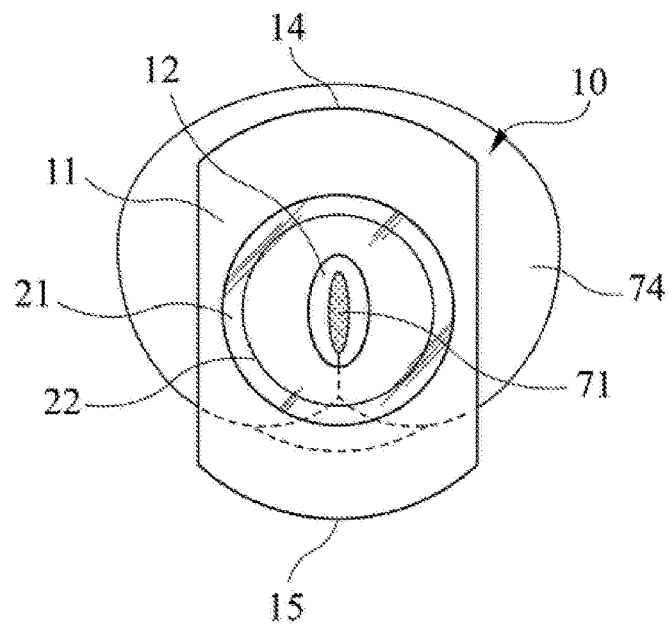
FIG. 3 is a schematic view showing one embodiment of the body fluid collection device of the present invention.

FIG. 3 shows another embodiment of the body fluid collection device 10 of the present invention. A front view of the glans penis 74 of the user is illustrated in FIG. 3. The collection film 21 is a transparent circular planar elastic film, and the distance between the arc shape top edge 14 of the fitting part 11 and the arc shape bottom edge 15 is greater than the distance between the two side edges of the fitting part 11. Considering the structure in which the distance between the two side edges of the fitting part 11 is small, when the user uses the body fluid collection device 10 as a male contraceptive device, the user's pleasure can be increased since the two sides of the glans penis 74 are exposed more.

Figure 4A:
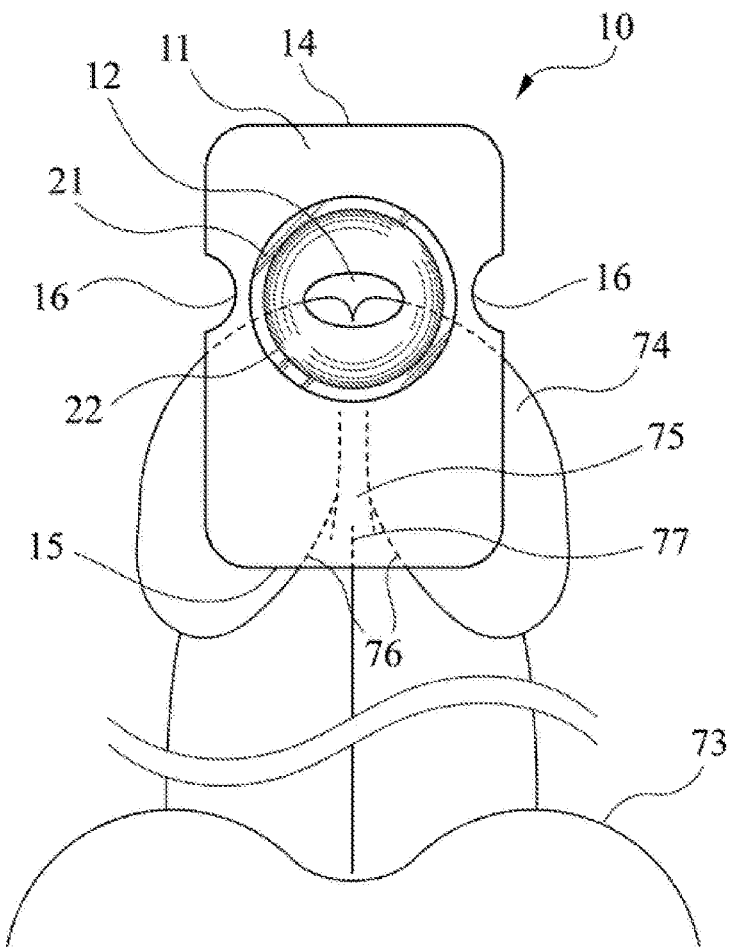
FIG. 4A is a schematic view showing one embodiment of the body fluid collection device of the present invention.
Figure 4B:
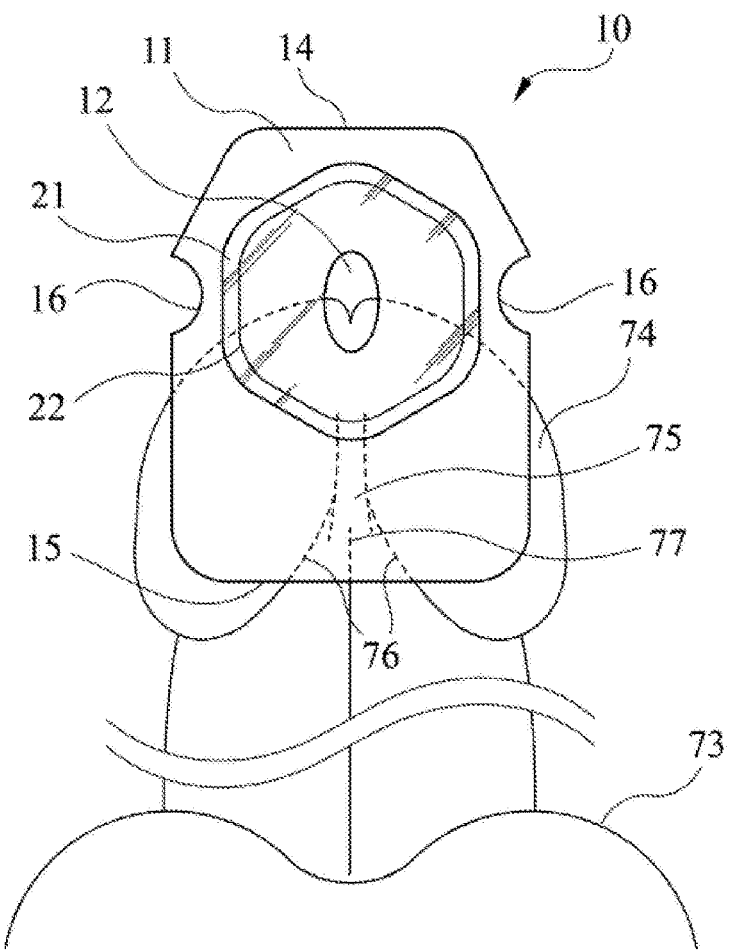
FIG. 4B is a schematic view showing one embodiment of the body fluid collection device of the present invention.

To make the fitting part 11 adhere more firmly to the glans penis 74, the edge of the fitting part 11 may have at least one notch, preferably an arc shape notch. When the body fluid collection device 10 is adhered to the glans penis 74 whose surface is curved, protruding wrinkles generated at the edge of the fitting part 11 can be avoided and therefore, impacts on the adhesion of the fitting are avoided. As shown in FIG. 4A, the collection film 21 is a transparent circular curved elastic film, and two arc shape notches 16 are provided at the alignment between the two side edges of the fitting part 11 and the opening 12 respectively. In addition, the surface of the penis where the frenulum 75 meets the corona glandis 76 adjacent to the scrotum 73 is uneven, and at the same time is also a region that receives the greatest frictional force caused during the piston motion. Accordingly, the part of the fitting part 11 from the opening 12 to the bottom edge 15 is longer than the part of the fitting part 11 from the opening 12 to the top edge 14, so that the bottom edge 15 can extend to adhere to the raphe of penis 77. In other words, when the fitting part 11 is substantially in a rounded rectangle (shown in FIG. 4A), the opening 12 is located on a long symmetry axis of the rounded rectangle (the long symmetry axis is in the vertical direction in FIG. 4A), but not on a shorter symmetry axis of the rounded rectangle (the short symmetry axis is in the horizontal direction in FIG. 4A). That is, the distances between the opening 12 and the two short sides of the rectangle (the two outer edges of the fitting part 11 on the long symmetry axis) are not equal, so that the fitting part 11 can be adhered more firmly and is not easy to peel off. The top edge 14 or the bottom edge 15 of the fitting part 11 may be linear, and is approximately perpendicular to the raphe of penis 77 in use. Since the linear top edge 14 or the bottom edge 15 is perpendicular to the direction of the piston motion, it can withstand more friction force caused during the piston motion than the edge of the circular arc, so that the fitting part 11 is less likely to be peeled off from the top edge 14 or the bottom edge 15. In addition, as shown in FIG. 4B, the edge of the rounded polygonal transparent collection film 21 is connected to the second surface of the fitting part 11 along a rounded regular hexagon, and the bottom edge 15 of the fitting part 11 may be longer than the top edge 14, so that the fitting part 11 is in a structure having a narrow top and a wide bottom. The part between the opening 12 and the bottom edge 15 is wider, so that the fitting part 11 can more firmly adhere to the meeting point of the frenulum 75 of the penis and the corona glandis 76 of the user. In other words, the fitting part 11 may be in a rounded polygon (the fitting part 11 disclosed in FIG. 4B is substantially hexagonal) having a symmetry axis (vertical direction in FIG. 4B) and a first side and a second side (the top edge 14 and the bottom edge 15 in FIG. 4B) perpendicular to the symmetry axis, the length of the first side is not equal to the length of the second side, and the opening 12 is located on the symmetry axis.

Figure 5A:
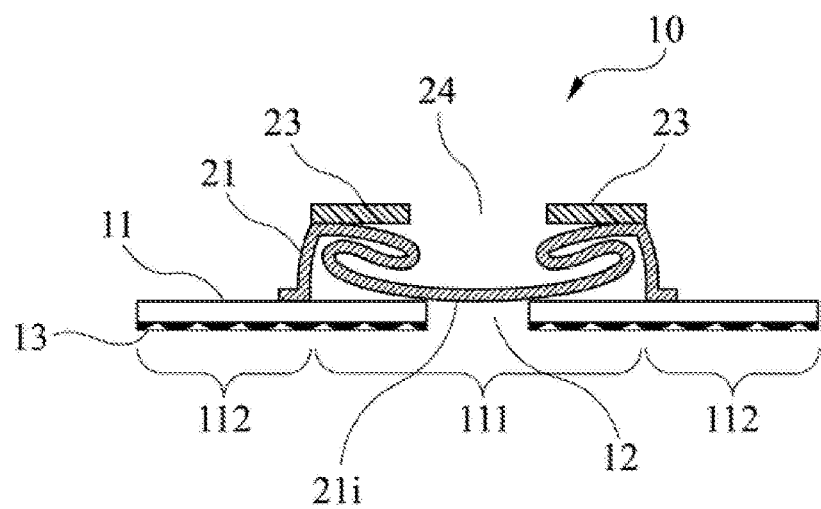
FIG. 5A is a schematic view showing one embodiment of the body fluid collection device of the present invention.
Figure 5B:
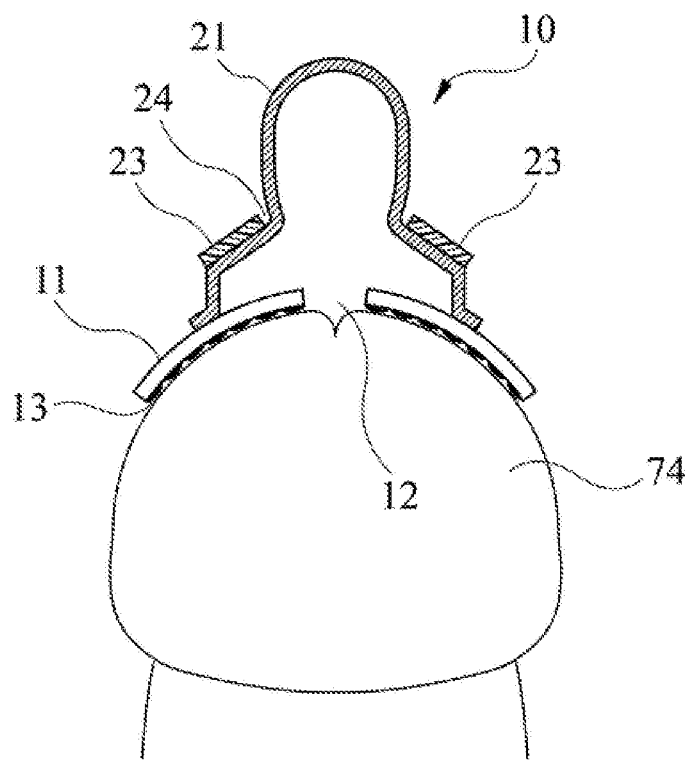
FIG. 5B is a schematic view showing one embodiment of the body fluid collection device of the present invention.

FIG. 5A is another embodiment of the body fluid collection device 10 of the present invention. The collection film 21 has a pocket structure. Before the body fluid collection device 10 is used, the closed end of the pocket structure is inverted or folded inward toward the center of the open end, so that the inner surface 21i of the closed end is close to the fitting part 11. A retaining part 23 may be further disposed on the outer side, and close to the open end, of the collection film 21. The retaining part 23 may be a planar or radially curved sheet and has at least one retaining part opening 24, and the outer edge of the retaining part 23 is connected to the outer side of the pocket structure at a position close to the open end. During the sexual behavior, the retaining part 23 can accommodate most of the folded-back collection film 21, thereby preventing the collection film 21 from being excessively pulled due to the piston motion, and allowing the collection film 21 to be folded outwards via the retaining part opening 24 due to receiving semen when the user ejaculates, so that the collection film 21 restores to the state before the folding back (shown in FIG. 5B).

Figure 6:
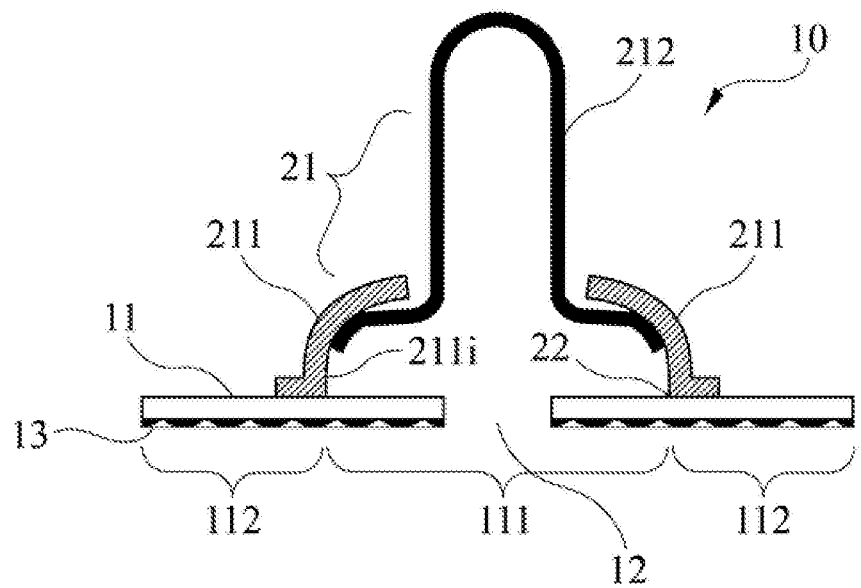
FIG. 6 is a schematic view showing one embodiment of the body fluid collection device of the present invention.

FIG. 6 is another embodiment of the present invention. The body fluid collection device 10 includes a fitting part 11, and a collection film 21 including an annular part 211 and a pocket part 212. The annular part 211 is a planar or radially curved annular film, and the outer edge of the annular part is the edge of the collection film 21. The pocket part 212 has an open end, and the open end has a circumference greater than the circumference of the inner edge of the annular part 211 and is connected to the inner surface 211i of the annular part 211. That is, there is a distance between the inner edge of the annular part 211 and the joint of the open end of the pocket part 212 and the inner surface 211i of the annular part 211. Therefore, the inner portion 111 of the fitting part 11, a part of the annular part 211, and the pocket part 212 constitute a storage space having an opening 12 and used for storing the prostatic fluid or semen of the user. The annular part 211 and the pocket part 212 may be made of the same or different materials, and have the same or different thicknesses.

Figure 7A:
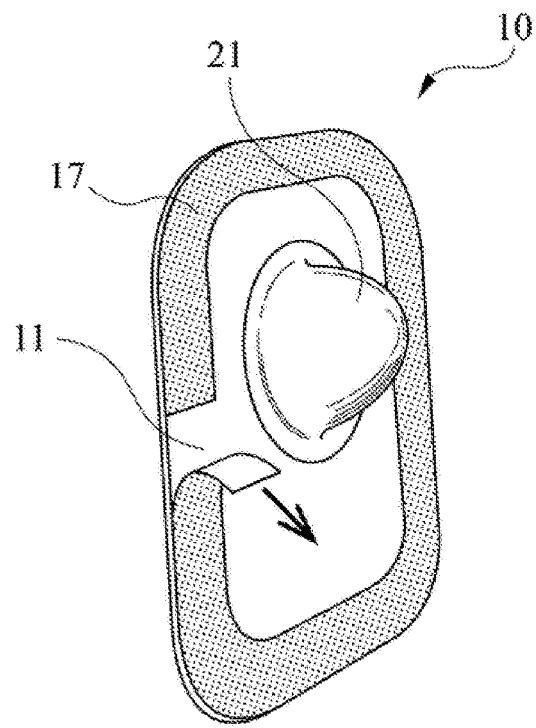
FIG. 7A is a schematic view showing one embodiment of the body fluid collection device of the present invention.
Figure 7B:
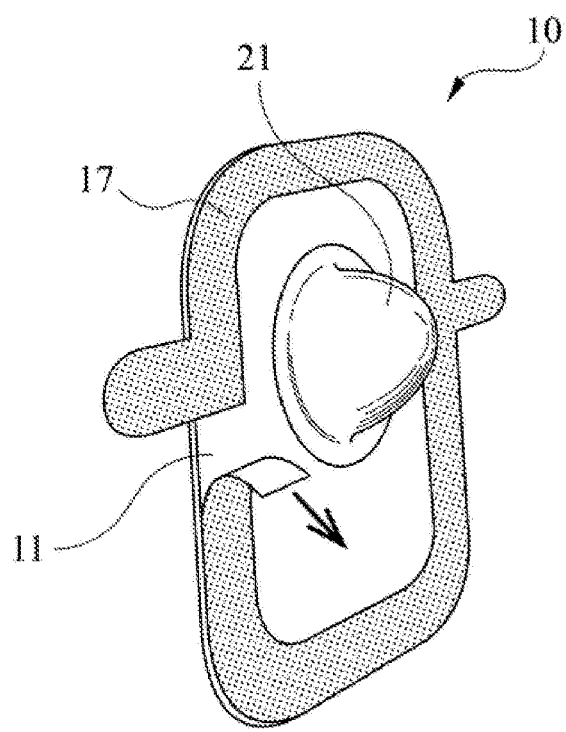
FIG. 7B is a schematic view showing one embodiment of the body fluid collection device of the present invention.

FIG. 7A shows one embodiment of the present invention. The body fluid collection device 10 may include a structure holding part 17 extending along the edge of the fitting part 11 as if a frame is provided on the fitting part 11 for holding the shape of the edge of the fitting part 11 before fitting, thereby avoiding generating wrinkles when the fitting part 11 is adhered to the glans penis 74 of the user. Since the structure holding part 17 is adhered to the second surface of the fitting part 11 by the weak adhesive, that is, the bonding force between the structure holding part 17 and the fitting part 11 is smaller than the bonding force between the fitting part 11 and the glans penis 74, the user does not peel the fitting part 11 from the glans penis 74 when the structure holding part 17 is removed. A part of the outer edge of the structure holding part 17 is further extendable to form at least one fin protruding from the fitting part 11 (shown in FIG. 7B) for the user to grip with fingers.

Figure 8:
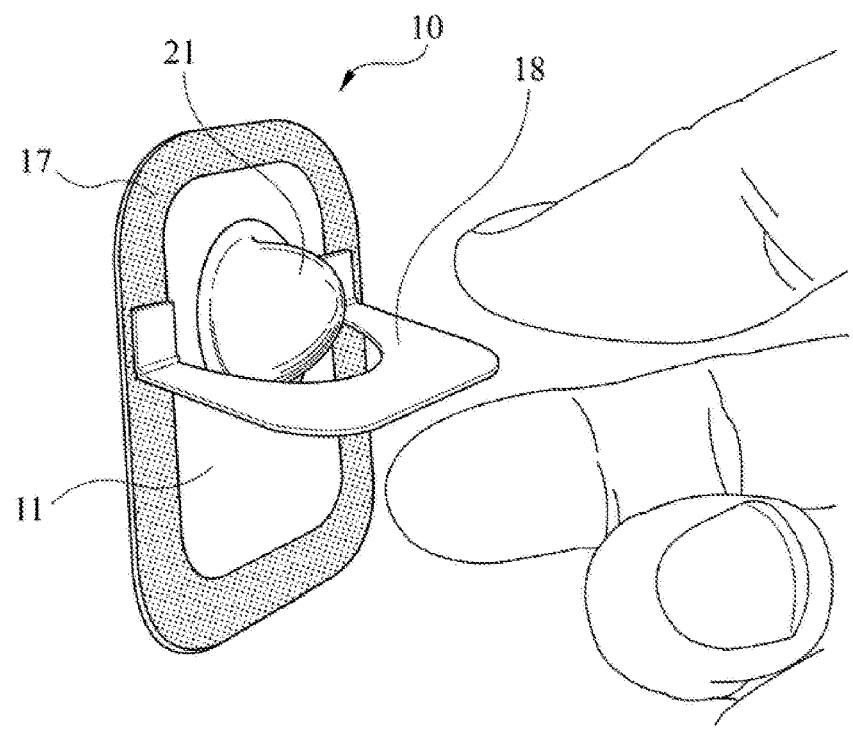
FIG. 8 is a schematic view showing one embodiment of the body fluid collection device of the present invention.

FIG. 8 shows one embodiment of the present invention. The body fluid collection device 10 includes a griping part 18 having at least one point connected to the structure holding part 17. The griping part 18 may be folded to be flattened to the fitting part 11 or the structure holding part 17, or pulled to a position at an angle of about 90 degrees with the fitting part 11 for the user to grip with fingers so as to adhere or adjust the body fluid collection device 10 or remove the structure holding part 17.

The above description is based on embodiments of the present invention, and the present invention is not limited thereto. The structures shown in the embodiments can also be used for collecting other body fluids such as urine.

Figure 9:
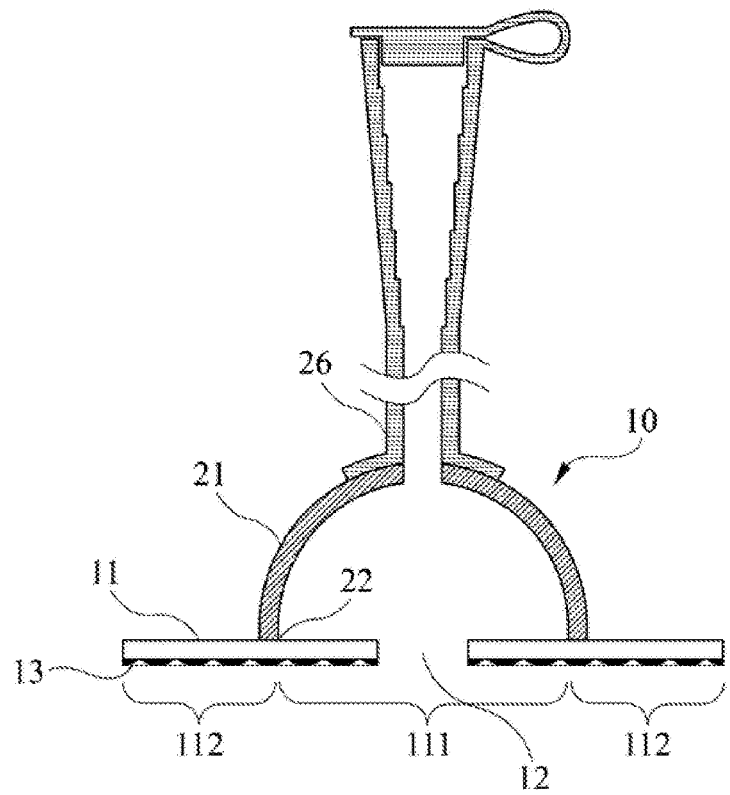
FIG. 9 is a schematic view showing one embodiment of the body fluid collection device of the present invention.

FIG. 9 shows one embodiment of the present invention, in which the collection film 21 has a pocket structure having a connecting hole in addition to an open end (defined by the edge of the collection film 21) connected to the fitting part 11. The connecting hole is connected to a drainage tube 26, and the end of the drainage tube 26 may be, but not limited to, a flared joint, and may be connected with a cover to close the flared joint, so that the body fluid (such as semen or urine) stored in the storage space can be introduced into a container (such as a test tube or a urine bag) at certain intervals.

The above description is merely illustrative, and not restrictive. Any equivalent modifications or changes without departing from the spirit and scope of the present invention are intended to be included within the scope of the appended claims.

SYMBOL DESCRIPTION 10 body fluid collection device
11 fitting part
111 inner portion
112 outer portion
12 opening
13 adhesive layer
14 top edge
15 bottom edge
16 arc shape notch
17 structure holding part
18 griping part
21 collection film
21i inner surface
211 annular part
211i inner surface
212 pocket part
22 connecting rim
23 retaining part
24 retaining part opening
26 drainage tube
71 urethra orifice
72 abdomen
73 scrotum
74 glans penis
75 frenulum
76 corona glandis
77 raphe of penis
F1 pressure
F2 pulling force
F3 pulling force.

What is claimed is:
1. A body fluid collection device, comprising:
a fitting part, which is a sheet having an opening and has a first surface and a second surface;
an adhesive layer disposed on the first surface of the fitting part; and
a collection film having an edge with a circumference greater than a circumference of the opening of the fitting part and connected to the second surface of the fitting part in a manner of surrounding the opening of the fitting part
wherein a joint of the edge of the collection film and the second surface of the fitting part has a width, an inner edge of the joint forms a connecting rim surrounding the opening, the connecting rim has a circumference greater than the circumference of the opening and there is a distance between the connecting rim and the circumference of the opening such that the fitting part is divided into an inner portion and an outer portion, the inner portion of the fitting part and the collection film constitute a storage space having the opening, and the storage space is capable of storing the body fluid of a user.

2. The body fluid collection device according to claim 1, wherein the body fluid collection device further comprises a structure holding part extending along the edge of the fitting part.

3. The body fluid collection device according to claim 2, wherein a part of an outer edge of the structure holding part is further extending outwards to form at least one fin protruding from the fitting part for the user to grip with fingers.

4. The body fluid collection device according to claim 2, wherein the body fluid collection device further comprises a gripping part having at least one point connected to the structure holding part and foldable to be flattened to the fitting part before use.

5. The body fluid collection device according to claim 1, wherein the collection film has a pocket structure, the pocket structure having an open end defined by the edge of the collection film.

6. The body fluid collection device according to claim 5, wherein the body fluid collection device further comprises:
a retaining part, which is a planar or radially curved sheet and is provided with at least one retaining part opening, an outer edge of the retaining part being connected to the outer side of the pocket structure close to the open end.

7. The body fluid collection device according to claim 1, wherein the edge of the collection film is connected to the second surface of the fitting part along a circle, an ellipse or a rounded regular polygon.

8. The body fluid collection device according to claim 7, wherein the opening of the fitting part is located at the center of the circle, the ellipse or the rounded regular polygon.

9. The body fluid collection device according to claim 1, wherein an edge of the fitting part has a notch.

10. The body fluid collection device according to claim 9, wherein the notch is an arc shape notch.

11. The body fluid collection device according to claim 1, wherein the collection film comprises:

an annular part, which is a planar or radially curved annular film, an outer edge of the annular part being the edge of the collection film; and
a pocket part having a pocket part open end, the pocket part open end being connected to an inner surface of the annular part,
wherein the pocket part open end of the pocket part has a circumference greater than the circumference of an inner edge of the annular part, and is connected to the inner surface of the annular part at a distance from the inner edge of the annular part.

12. The body fluid collection device according to claim 1, wherein the body fluid collection device further comprises a drainage tube, wherein the collection film has a pocket structure, the pocket structure having a connecting hole and an open end defined by the edge of the collection film, and the drainage tube being connected to the connecting hole.

13. The body fluid collection device according to claim 1, wherein the collection film is a planar or curved elastic film.

14. The body fluid collection device according to claim 1, wherein the fitting part is a planar sheet or a curved sheet.

15. The body fluid collection device according to claim 1, wherein the edge of the collection film is not in contact with an outer edge of the fitting part.

16. The body fluid collection device according to claim 1, wherein the opening is located on a long symmetry axis of the fitting part, and distances between the opening and two outer edges of the fitting part on the long symmetry axis are not equal.

17. The body fluid collection device according to claim 1, wherein the shape of the fitting part is a circle, an ellipse or a rounded polygon.

18. The body fluid collection device according to claim 1, wherein the constituent material of the adhesive layer comprises a pressure-sensitive adhesive.

19. The body fluid collection device according to claim 1, wherein the edge of the collection film and the fitting part are integrally formed so as to be connected.

20. The body fluid collection device according to claim 1, wherein the body fluid collection device further comprises a drainage tube, wherein the collection film having a connecting hole and the drainage tube is connected to the connecting hole.

* * * * *